United States Patent [19]

Habenstein et al.

[11] Patent Number: 4,563,421
[45] Date of Patent: Jan. 7, 1986

[54] METHOD FOR DETERMINING THE PRESENCE OF ENDOHYDROLASE IN A LIQUID AND COMPOSITION THEREFOR

[75] Inventors: Klaus Habenstein, Lahntal; Helmut Kohl, Wetter, both of Fed. Rep. of Germany

[73] Assignee: Hoechst Aktiengesellschaft, Frankfurt, Fed. Rep. of Germany

[21] Appl. No.: 555,435

[22] Filed: Nov. 25, 1983

Related U.S. Application Data

[62] Division of Ser. No. 225,647, Jan. 16, 1981, abandoned.

[30] Foreign Application Priority Data

Jan. 19, 1980 [DE] Fed. Rep. of Germany ....... 3001878

[51] Int. Cl.$^4$ ..................... A61K 31/715; I12Q 1/34
[52] U.S. Cl. ............................... 435/18; 435/22; 435/4; 536/1.1; 536/2; 536/18.6; 536/18.7; 536/95; 536/98; 536/102; 536/103; 536/111; 536/112; 536/120; 514/57; 514/60; 252/408.1
[58] Field of Search ................. 435/18; 536/2, 1.1, 536/95, 98, 102, 103, 111, 112, 120, 18.7, 18.6; 424/180; 514/57, 60

[56] References Cited

U.S. PATENT DOCUMENTS

| | | | |
|---|---|---|---|
| 2,599,620 | 6/1952 | Filbert | 536/120 |
| 3,676,303 | 7/1972 | Ingelman et al. | 435/18 |
| 3,919,107 | 11/1975 | Thompson | 536/103 |
| 4,000,127 | 12/1976 | Cornelissens et al. | 536/2 |
| 4,020,268 | 4/1977 | Nishikawa et al. | 536/112 |
| 4,076,930 | 2/1978 | Ellingboe et al. | 536/112 |

*Primary Examiner*—Johnnie R. Brown
*Attorney, Agent, or Firm*—Curtis, Morris & Safford

[57] ABSTRACT

What are disclosed are polysaccharide derivatives of the formula

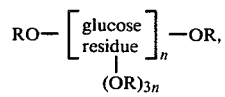

in which n denotes a number from 100 to 12,500 and R denotes hydrogen, a carboxyalkyl or hydroxyalkyl group with 1 to 5 carbon atoms in the alkyl radical or a detectable molecular group, any combination of the (3n+2) R radicals being possible, but at least one R being a carboxyalkyl or hydroxyalkyl group and at least one R being a detectable molecular group, and a process for their preparation and their use for the determination of endohydrolases, in indicator paper and for the detection of metabolites in biological liquids, are described.

6 Claims, No Drawings

METHOD FOR DETERMINING THE PRESENCE OF ENDOHYDROLASE IN A LIQUID AND COMPOSITION THEREFOR

This application is a division, of application Ser. No. 225,647, filed Jan. 16, 1981, now abandoned.

The present invention relates to derivatives of carboxyalkylated or hydroxyalkylated polysaccharides consisting of glucose units, a process for their preparation, their use in analysis methods and agents containing these derivatives.

It is known, from Industrial and Engineering Product Research and Development 8, 77–79 (1969), to react starch with isatoic anhydride so that a starch which contains hydroxyl groups esterified with anthranilic acid is formed, carbon dioxide being split off.

The present invention relates to derivatives, which are soluble in polar solvents, of carboxyalkylated or hydroxyalkylated polysaccharides which consist of glucose units and can be represented schematically as follows:

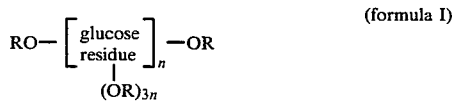

(formula I)

in which n denotes a number from 100 to 12,500 and R denotes hydrogen, a carboxyalkyl or hydroxyalkyl group with 1 to 5 carbon atoms in the alkyl radical or a detectable molecular group, any combination of the (3n+2) R radicals being possible, but at least one R being a carboxyalkyl or hydroxyalkyl group and at least one R being a detectable molecular group.

The term "detectable molecular group" comprises chromophoric, chromogenic, fluorescent or radioactive groupings.

The derivatives according to the invention are split hydrolytically by endohydrolases which hydrolyze polysaccharides. They can therefore be used as substrates for the detection and for the determination of such hydrolases.

Since it has furthermore been found that the soluble derivatives according to the invention become insoluble as a result of drying on a carrier, they can also be used for the preparation of carrier-bonded indicators which do not bleed.

It is possible to diagnose some dangerous illnesses via determination of the amylase activity in serum or urine. There is thus a need for simple tests which can be carried out rapidly and which enable this group of polysaccharide-hydrolyzing endohydrolases to be detected with good reproducibility.

Methods for the determination of such enzymes are known; these methods are based on determining the sugar formed by the degradation of starch.

In other processes, the amount of dyestuff or other molecular groups which are split off, by enzymatic action, from starch to which a dyestuff or other molecular groups are bonded is measured.

Thus, a process in which a "dye-starch" is utilized as the substrate is known (British Patent Specification No. 1,489,059 and L. Fridhandler, J. E. Berk and S. Take, Digestive Diseases (1979) 15 (11), 1,039). In this process, water-soluble, colloidal dye-starch complexes are fixed onto absorbent carriers in several steps by a procedure in which, after initial impregnation, the substrate is precipitated on the carrer and, in a further step, the carrier is purified by removal of excess soluble substrate. It is evident that these three process steps are troublesome and, because of interaction, "fixing-purifying" must lead to tests which are difficult to reproduce, inter alia as a result of entraining effects.

The follwowing substrates are used in other processes: a water-soluble "dye-starch" which consists of a water-soluble starch or starch component and a dyestuff covalently bonded thereto (U.S. Pat. No. 3,579,322; and British Patent Specification No. 1,167,083), or a water-insoluble "dye-starch" which consists of a water-insoluble starch or starch component and a dyestuff covalently bonded thereto (H. Rinderknecht, P. Wilding and B. J. Haverback, Experimenta 23 (1967), 805 and German Auslegeschrift No. 1,940,869) or of a water-soluble starch or starch component and detectable molecular groups covalently bonded thereto, the starch having been rendered water-insoluble by crosslinking (German Offenlegungsschrift No. 1,901,517 and Japanese Preliminary Published Specification No. 75 21,789 and 75 57,697).

There are also great problems in applying a water-insoluble dye-starch complex in a suitable form to a reagent carrier, since this carrier must already be incorporated into the paper during the production thereof.

Fixing soluble dye-starch onto a carrier which has already been impregnated therewith requires additional process steps, during which, furthermore, it is not possible to prevent partial bleeding.

The present invention was thus first based on the object of developing a substrate, which can be processed without problem and uniformly, for a simple reliable process for the detection and for the determination of endohydrolases.

This object is achieved with a carboxyalkylated or hydroxyalkylated polysaccharide onto which a detectable molecular group can be bonded. The polysaccharide is a substrate for endohydrolases which hydrolyze polysaccharides.

Surprisingly, it has been found, in fact, that carboxyalkylated or hydroxyalkylated polysaccharides built up from glucose units and derived analogs thereof with detectable molecular groups are attacked by polysaccharide-hydrolyzing endohydrolases, have a good solubility in aqueous solvents and polar aprotic solvents and, when applied to naturally occurring absorbent carriers in aqueous solution, can be fixed, by simple drying, in an almost water-insoluble but swellable form.

These properties, the sum of which is achieved neither by naturally occurring starches or starch products nor by other starch derivatives, render carboxyalkyl-starches and hydroxyalkyl-starches, especially those covalently bonded to detectable molecular groups, a suitable substrate base for indicator paper, but in particular for diagnostic agents for the detection of endohydrolases.

The invention accordingly also relates to an agent for the detection and for the determination of endohydrolases, which contains a compound of the formula I, from which, however, the detectable molecular group can be absent.

A preferred embodiment of the diagnostic agent according to the invention consists of a naturally occurring absorbent carrier, for example cellulose, which contains the substrate according to the invention and, if appropriate, a buffer salt, an accelerator or inhibitor and a detergent. The absorbent, impregnated carrier is arranged on a reagent carrier in a manner such that, when amylase is present, the chromogenic compound released can be detected by a simple chromatographic step.

Particularly suitable substrates are carboxyalkylated or hydroxyalkylated polysaccharides of the amylose, amylopectin, dextran or dextrin type, which can be covalently bonded to detectable molecular groups.

Compounds of the formula I in which n is a number from 100 to 12,500 and R is hydrogen, a carboxyalkyl or hydroxyalkyl group with 1–5 carbon atoms in the alkyl radical or a detectable molecular group are suitable.

Detectable molecular groups can be dyestuffs chemically bonded to the polysaccharide, such as, for example, Remazol®, Cibachron®, Drimaren®, Procion® or Lewafix® dyestuffs. However, detectable molecular groups can equally be compounds which are chemically bonded to the polysaccharide and analogs thereof which additionally contain groupings which can be detected by a chemical method.

Particularly preferred embodiments of the formula I are those in which n is a number from 350 to 12,500 and R is hydrogen, a carboxyalkyl or hydroxyalkyl group with 1–3 carbon atoms in the alkyl radical or a detectable molecular group.

Finally, compounds in which n is a number from 600 to 6,000 and R is hydrogen, a carboxyalkyl or hydroxyalkyl group with 1–2 carbon atoms in the alkyl radical or a detectable molecular group are of particular interest.

In the case of covalent bonding of the detectable molecular groups, the reactivity of the hydroxyl groups present in a polysaccharides can be utilized for etherification or esterification. For example, reactive dyestuffs (in particular Remazol dyestuffs) can be bonded to carboxymethyl-starch or hydroxyalkyl-starch by the customary processes for dyeing paper or cotton. Using the reactive groupings utilized for covalent bonding in these types of dyestuffs (in this context, see German Auslegeschrift 1,293,362, page 1, and J. Panchartek et al., Coll. Czech., Chem. Commen. (1960) 25, 2,783–2,799), other chromogenic groups or molecular radicals which are fluorescent or contain radioisotopes can equally well be bonded onto the polysaccharides on which the compounds of the formula I are based.

In principle, the choice of buffer salts is not critical if the incompatibilities of the particular system, which are familiar to the expert, are taken into consideration (for example inhibition of α-amylase by EDTA or citrate and salicylic acid). On the other hand, such interactions can be utilized to adjust the system (for example the detection limits). The pH value can be varied within limits, and will approximately be in the range known as optimum for the particular enzyme (for example pH 6.9–7.2 for α-amylase and pH 4.4–4.6 for β-amylase). Sodium halides, in particular sodium chloride, in concentrations of 10–100 mmoles/l are known as accelerators.

Examples of inhibitors have already been mentioned (EDTA, citrates and salicyclic acid). Some proteins isolated from cereal seeds are known as other inhibitors with a very powerful action (German Auslegeshrift No. 2,003,934).

The process for the carboxymethylation of polysaccharides which is described in U.S. Pat. No. 2,599,620, Examples 1 and 2, can be used, for example, for the preparation of a substrate. Other carboxyalkylated polysaccharides can be prepared in a corresponding manner. Hydroxyalkyl-starch is commercially available.

Detectable molecular radicals can be introduced as indicated by H. Rinderknecht, P. Wilding and J. B. Haverback, Experiments 23, 805 (1967) and German Auslegeschrift No. 1,940,869, German Offenlegungsschrift No. 1,901,517 and German Offenlegungsschrift No. 2,801,455.

For example, carboxymethyl-starch can be reacted, at a pH value greater than 7, with a dyestuff which contains, for example, sulfatoethyl sulfone groups (SES), that is to say the structural element $—SO_2CH_2—CH_2OSO_3H$. If appropriate, an alkali metal phosphate is also added to the batch. After several hours at room temperature, the batch is neutralized and the dye-starch complex is isolated.

The invention furthermore relates to the use of compounds of the formula I for indicator papers, powders and films. These are particularly distinguished by the fact that they do not bleed on contact with water.

In German Auslegeschrift No. 1,256,445, molecules with chromophoric groupings and reactive centers, such as, for example, the oxyethylsulfonic acid radical, are bonded chemically to cellulose or regenerated cellulose in order to prepare non-bleeding indicator paper.

In German Auslegeschrift No. 2,436,257, a process is described in which the indicators employed have substantive properties, that is to say the chemical compounds are absorbed onto cotton or similar natural carriers so that they no longer bleed. This paper has disadvantages.

The first process does not give papers which fulfil practical requirements (German Offenlegungsschrift No. 1,698,247). Furthermore, according to our experience, such indicator paper can only be prepared with difficulty, since troublesome bulk-dyeing of cellulose must first be carried out in order then to produce paper therefrom, and this leads to a pollution of the environment by large amounts of effluent. In addition, production of indicator paper is only economic if large amounts of paper are produced. Papers produced according to the second process have only a limited fastness to bleeding. Especially in the strongly basic ranges above pH 10, they have a severe tendency to bleed. For their production, it is necessary to synthesize particular chemicals in an expensive manner, some of these chemicals only being soluble in troublesome solvents, such as pyridine or even hydrochloric acid. This indicator paper must also be produced by a troublesome bulk-dyeing of cellulose and casting to form sheets.

The aim of the present invention was also to indicate a simple way of preparing non-bleeding indicator paper. In addition, it should be possible to prepare this paper in as many forms as desired, and also in small amounts and without high costs.

Compounds of the formula I are used to solve the given problem. These compounds, if appropriate purified by one of the methods customary in chemistry, can be applied in the form of an aqueous, optically clear solution to a carrier, preferably an absorbent material, in particular cellulose. After drying, the dye complex adheres so firmly that no bleeding of the dyestuffs in aqueous or organic-aqueous solutions can be observed.

Suitable compounds of the formula I can be obtained, for example, by reacting pH indicator dyestuffs with a reactive anchor with a polysaccharide. Such a compound can be applied to a carrier matrix, for example cellulose. For simplicity, paper is immersed in the aqueous solution of the compound, or the impregnating solution is applied to the matrix in a known manner by means of a doctor blade. After a final drying operation, the impregnated paper is ready to use. To prepare the dye-starch complexes, the reactive dyestuff and starch derivatives are reacted as described above.

The advantages of indicator paper prepared in this manner are, for example, that it can be prepared in any desired amount, even in a small amount, and that expensive units for the production of paper are not required.

The components of the formula I can also be isolated as a solid powder, which can then be further processed as desired. Thus, after adding binders and adhesives, it is possible to prepare, for example, indicator tablets, and to obtain indicator films by incorporating the powder in a plastic matrix. They are accordingly generally suitable for producing films and tablets using synthetic or naturally occurring sheet-forming polymers.

The new indicator paper can be used, for example, as pH-indicator paper or as a rapid diagnostic agent for investigating solutions. Thus, it is possible to obtain, according to the process described in German Offenlegungsschrift No. 2,141,487, compounds of the formula I which can be used, for example, for the detection of nitrite, bilirubin and urobilinogen in biological fluids or as an oxidation indicator. They can be used generally for the determination of chemical parameters in liquids, above all in so-called rapid diagnostic agents.

The examples below are intended to illustrate the invention in more detail:

EXAMPLE 1

Preparation of a carboxymethylated dye-starch 5 g of sodium chloride, 0.1 g of tetrasodium diphosphate, 1 g of one of the reactive dyestuffs mentioned below and 2.5 g of CM-starch (degree of substitution: 0.13) are dissolved in 100 ml of water.

1.5 ml of 10 N sodium hydroxide solution are added. The solution is stirred at room temperature for 2 hours and then diluted with 100 ml of phosphate buffer (70 mmoles, pH 7), and the dye-starch is precipitated with 800 ml of methanol and washed three times with 100 ml of methanol each time. If necessary, the resulting dried product is comminuted. Other carboxymethylated dye-starches and hydroxyalkylated dye-starches can be prepared analogously. Suitable reactive dyestuffs are, for example, Remazol ®, Cibachron ®, Drimaren ®, Procion ® and Lewafix ® dyestuffs.

EXAMPLE 2

Preparation of a test paper (a) 200 cm² of base indicator paper (140 g/m²) are impregnated with the following solution and dried: 2.5 g of CM- (or HA-) dye-starch, 2.5 g of sodium chloride and 0.1 g of sodium azide, dissolved in 100 ml of phosphate buffer (70 mmoles, pH 7).

The resulting paper can be used as follows:

One drop of a sample containing amylase is placed on a piece of the test paper and is allowed to act for about 2 minutes and the paper is rinsed with distilled water and dabbed dry. The amylase content can be seen from the degree of washing out (bleaching) of the color.

(b) The solution of Example 2(a) can be applied to paper in the form of one or more streaks and the paper can be cut into manageable (about 5–10 mm wide) strips at right-angles to the direction of the streaks. One end of a strip thus obtained is immersed in the amylase-containing sample. The liquid chromatographs through the dye-starch zone or zones running at right-angles, and thereby entrains the dyestuff which has been released as a result of attack by amylase. Different amylase contents can be detected either by different depths of color of the liquid chromatographing further (Table I) or by the number of streaks removed (Table II).

TABLE I

| (SCE = Street-Close units) | | | | | | | | |
|---|---|---|---|---|---|---|---|---|
| 0 | 25 | 50 | 100 | 200 | 400 | 800 | 2,400 | 6,400 |
| | | | | SCE/dl | | | | |
| 0 | 1 | 1 | 2 | 3 | 4 | 5 | 6 | 7 |

The increasing sequence of figures indicates the different color intensities in the chromatographing liquid after passage through the dye-starch zone.

TABLE II

| (SCE = Street-Close units) | | | | | | | | | |
|---|---|---|---|---|---|---|---|---|---|
| 0 | 25 | 50 | 100 | 200 | 400 | 800 | 1,600 | 3,200 | 6,400 |
| | | | | | SCE/dl | | | | |
| 10 | 10 | 10 | 10 | 8 | 6 | 4 | 2 | 1 | — |

The figures give the number of lines still present after a reaction time of 5 minutes.

EXAMPLE 3

The use of an accelerator or inhibitor enables an activity range which is to be detected to be established.

(a) 5 g/l of Monflor ®51 (Serva 29842, Heidelberg) and 2 g/l of albumin are added, as accelerators, to a solution according to Example 2(a) and paper is prepared analogously to Example 2(b). Table III shows the test result.

TABLE III

| 0 | 25 | 50 | 100 | 200 | 400 | 800 | 1,600 | 3,200 | 6,400 |
|---|---|---|---|---|---|---|---|---|---|
| | | | | | SCE/dl | | | | |
| 10 | 10 | 10 | 9 | 7 | 5 | 3 | 1 | — | — |

The figures give the number of lines still present after a reaction time of 5 minutes.

(b) 50 ml/l of an amylase inhibitor obtained according to German Auslegeschrift No. 2,003,934 are dissolved in a solution according to Example 1. The solution is processed analogously to Example 3(a). Table IV shows the test results.

TABLE IV

| 0 | 25 | 50 | 100 | 200 | 400 | 800 | 1,600 | 3,200 | 6,400 |
|---|---|---|---|---|---|---|---|---|---|
| | | | | | SCE/dl | | | | |
| 10 | 10 | 10 | 10 | 10 | 9 | 8 | 6 | 5 | 3 |

The figures give the number of lines still present after a reaction time of 5 minutes.

EXAMPLE 4

Preparation of pH-paper

Non-bleeding pH-paper is obtained according to Example 1 when the indicators listed in the following table are employed.

| Indicator | Change in color | pH range |
|---|---|---|
| Remazol Brilliant Orange BR | orange to blue-red | 10–12 |
| Cibachron Orange PP | orange to brown | 10–13 |
| Remazol Yellow FG | yellow to brown | 10–14 |
| 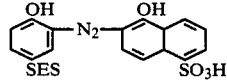 | red to blue | 5–8 |
| | blue to orange | 10–13 |

-continued

| Indicator | Change in color | pH range |
|---|---|---|
| SES―⟨⟩―N₂―⟨⟩―N(R)(R₁) | yellow to red | 3–1 |
| SES―⟨⟩―N₂―⟨⟩―N(R₁)(R₁) | orange to carmine red | 5–2 |

SES: —SO₂—CH₂—CH₂—OSO₃H
R: —CH₂—CH₃
R₁: —(CH₂)₂OSO₃H

The use value of the paper can be improved further by additionally using aluminum sulfate or wetting agents (for example quaternary ammonium compounds).

EXAMPLE 5

Indicator paper for clinical-chemical detection methods

An aromatic amine, for example 2-bromoaniline, is bonded to a carboxyalkylated or hydroxyalkylated starch via a sulfatoethyl sulfone group, according to Example 1. The purified indicator-starch complex is then diazotized. The diazonium salt formed is applied to chromatography paper, together with buffers and stabilizers. After drying, this system is suitable for the detection of bilirubin in body fluids.

Paper for the detection of urobilinogen in body fluids is prepared analogously.

Furthermore, an aniline-starch complex can be applied to chromatography paper together with organic acids and a coupler, such as β-naphthylamine. This paper can then be used as an agent for the detection of nitrite.

We claim:

1. An indicator for determining the presence of an endohydrolase, said indicator comprising a cellulose carrier impregnated with an adherent compound fixed onto said carrier by simple drying, which compound is a water soluble carboxyalkylated or hydroxyalkylated starch wherein the alkyl groups have from 1 to 5 carbon atoms, said starch having a dye bonded thereto, said compound being susceptible to enzymatic cleavage to release said dye therefrom when said indicator is contacted with an endohydrolase.

2. An indicator as in claim 1 wherein said compound is hydroxylalkylated starch.

3. An indicator as in claim 1 wherein said compound is carboxyalkylated starch.

4. An indicator as in claim 1 wherein said compound is carboxymethylated starch.

5. A method for determining the presence of an endohydrolase in a liquid, which method comprises contacting said liquid with an indicator as in claim 1, whereby dye groups are enzymatically cleaved in the presence of an endohydrolase, and detecting the cleaved dye groups.

6. A method as in claim 5 wherein said liquid is a biological fluid containing a metabolite which is an endohydrolase.

* * * * *

UNITED STATES PATENT AND TRADEMARK OFFICE
CERTIFICATE OF CORRECTION

PATENT NO. : 4,563,421

DATED : January 7, 1986

INVENTOR(S) : Habenstein et al.

It is certified that error appears in the above-identified patent and that said Letters Patent is hereby corrected as shown below:

In heading [73] assignee, change "Hoechst Aktiengesellschaft, Frankfurt am Main, Federal Republic of Germany" to --Behringwerke Aktiengesellschaft, Marburg, Federal Republic of Germany--.

Signed and Sealed this

Twenty-sixth Day of August 1986

[SEAL]

Attest:

DONALD J. QUIGG

Attesting Officer

Commissioner of Patents and Trademarks